United States Patent
Farine (10) Patent No.: US 9,877,797 B2
(45) Date of Patent: Jan. 30, 2018

(54) DENTAL OR SURGICAL COMPRESSED AIR HANDPIECE AND TURBINE FOR SUCH A HANDPIECE

(71) Applicant: Bien-Air Holding SA, Bienne (CH)

(72) Inventor: Laurent Farine, Moutier (CH)

(73) Assignee: Bien-Air Holding SA, Bienne (CH)

( * ) Notice: Subject to any disclaimer, the term of this patent is extended or adjusted under 35 U.S.C. 154(b) by 0 days.

(21) Appl. No.: 14/533,726

(22) Filed: Nov. 5, 2014

(65) Prior Publication Data

US 2015/0157420 A1    Jun. 11, 2015

(30) Foreign Application Priority Data

Dec. 9, 2013   (EP) .................................. 13196222

(51) Int. Cl.
  *A61C 1/05*   (2006.01)
  *A61C 1/12*   (2006.01)
  *A61B 17/16*  (2006.01)

(52) U.S. Cl.
  CPC ............. *A61C 1/05* (2013.01); *A61C 1/12* (2013.01); *A61B 17/1628* (2013.01)

(58) Field of Classification Search
  CPC .. A61C 1/05; A61C 1/18; A61C 1/185; A61C 1/12; A61B 17/1628
  See application file for complete search history.

(56) References Cited

U.S. PATENT DOCUMENTS

| | | | |
|---|---|---|---|
| 3,210,848 A * | 10/1965 | Bizzigotti | A61C 1/05 384/110 |
| 3,893,242 A | 7/1975 | Lieb et al. | |
| RE30,340 E * | 7/1980 | Borden | A61C 1/05 433/126 |
| 4,320,927 A | 3/1982 | Sertich | |
| 4,470,813 A * | 9/1984 | Thorburn | A61C 1/05 416/200 R |
| 4,941,828 A * | 7/1990 | Kimura | A61C 1/05 433/114 |
| 5,286,194 A | 2/1994 | Horiuchi et al. | |
| 5,562,446 A * | 10/1996 | Matsui | A61C 1/05 415/904 |
| 2009/0061384 A1* | 3/2009 | Thomssen | A61C 1/05 433/132 |
| 2011/0281232 A1 | 11/2011 | Brandner et al. | |

OTHER PUBLICATIONS

European Search Report issued in corresponding application EP 13 19 6222.7, dated May 7, 2014.

* cited by examiner

*Primary Examiner* — Rex R Holmes
(74) *Attorney, Agent, or Firm* — Oblon, McClelland, Maier & Neustadt, L.L.P.

(57) ABSTRACT

Compressed air handpiece including a handle connected to a head housing a turbine. The turbine includes a moving wheel from a periphery of which extends a plurality of blades which define an outer diameter of the moving wheel. The handpiece also includes injection means, whose function is to direct onto the blades of the moving wheel a compressed air flow whose pneumatic energy is converted into kinetic energy when the compressed air flow strikes the blades of the moving wheel. The injection means take the form of an independent insert inside which is arranged a compressed air flow feed pipe and which is mounted inside the handle of the handpiece.

25 Claims, 7 Drawing Sheets

DENTAL OR SURGICAL COMPRESSED AIR HANDPIECE AND TURBINE FOR SUCH A HANDPIECE

This application claims priority from European Patent Application No. 13196222.7 filed Dec. 9, 2013 the entire disclosure of which is incorporated herein by reference.

FIELD OF THE INVENTION

The present invention concerns a dental or surgical compressed air handpiece and a turbine for such a handpiece. The present invention concerns, in particular, a compressed air handpiece having increased power.

BACKGROUND OF THE INVENTION

The present invention concerns the field of handpieces for dental or surgical use. There are two families of handpieces: contra-angle handpieces which are equipped with an electrical motor and handpieces which include a turbine driven by compressed air.

We are concerned here with compressed air handpieces. In very simple terms, these compressed air handpieces include a head which houses a turbine. This turbine includes a compressed air feed pipe and a moving wheel provided with a plurality of regularly spaced blades at the periphery thereof. The feed pipe is used to force onto the turbine blades a compressed air flow whose pneumatic energy is converted into kinetic energy when the compressed air flow strikes the blades of the moving wheel.

Figure 1:
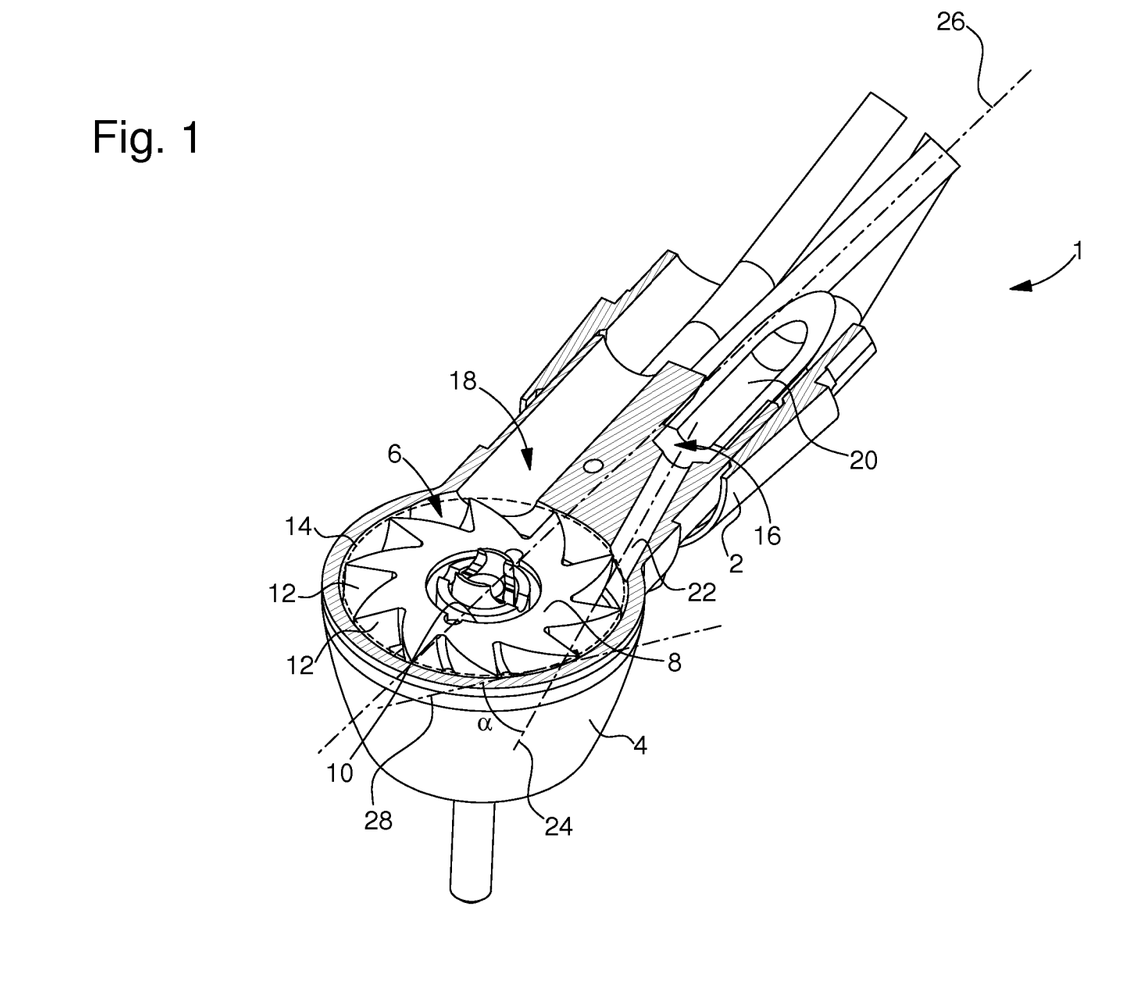
FIG. 1, already mentioned, is a perspective, cross-sectional view on a horizontal plane longitudinally intersecting the handle and the head of a compressed air handpiece according to the prior art.

FIG. 1 annexed to the present Patent Application is a perspective, cross-sectional view on a horizontal plane longitudinally intersecting the handle and the head of a compressed air handpiece according to the prior art. Designated as a whole by the general reference numeral 1, this handpiece includes a handle 2 which is connected to a head 4 which houses a turbine 6. Turbine 6 includes a moving wheel 8 from a periphery 10 of which extends a plurality of blades 12, which define an outer diameter 14 of moving wheel 8.

Handpiece 1 also includes injection means whose function is to direct onto blades 12 of moving wheel 8 a compressed air flow whose pneumatic energy is converted into kinetic energy when the compressed air flow strikes blades 12 of moving wheel 8. The compressed air injection means are formed of a compressed air feed pipe 16 which is machined in handle 2 of handpiece 1 using conventional techniques. Further, an air discharge pipe 18 is also machined by conventional techniques in handle 2 of handpiece 1, substantially parallel to and remote from compressed air feed pipe 16.

An examination of FIG. 1 reveals that compressed air feed pipe 16 is formed of a first and a second rectilinear pipe, respectively 20 and 22, arranged in the extension of each other, the longitudinal axis of symmetry 24 of second rectilinear pipe 22 extending slightly slantwise relative to longitudinal axis of symmetry 26 of handle 2 of handpiece 1 and making a non-zero angle a with the tangent 28 to outer diameter 14 of moving wheel 8. It is clear that it is difficult to envisage machining compressed air feed pipe 16 in a direction which would tend to move closer to the tangent 28 to outer diameter 14 of moving wheel 8 without risking piercing air discharge pipe 18 or having to reduce the diameter of pipe 18.

A recurrent problem facing designers of compressed air handpieces lies in the conversion efficiency between the pneumatic energy of the compressed air and the kinetic energy of the moving turbine wheel. Indeed, the mechanical power that the compressed air handpiece can deliver depends on this conversion efficiency. This conversion efficiency is closely connected, in particular, to the drop in pressure between the pressure of the compressed air which penetrates the head of the handpiece, and the pressure of the air leaving the head of the handpiece after the compressed air has struck the turbine blades. Indeed, the greater the pressure drop, the better the conversion between pneumatic energy and kinetic energy. The conversion efficiency between pneumatic energy and kinetic energy is also improved if the air flow occurs with minimal turbulence and thus minimal losses. It is also sought to reduce the operating noise of compressed air handpieces and to prevent, as far as possible, the compressed air intended to activate the turbine from escaping into the patient's mouth.

SUMMARY OF THE INVENTION

It is an object of the present invention to answer the aforementioned objects in addition to others by providing in particular a timepiece providing higher mechanical power.

The present invention therefore concerns a compressed air handpiece including a handle, which is connected to a head, which houses a turbine, the turbine including a moving wheel from a periphery of which extend a plurality of blades which define an outer diameter of the moving wheel, the handpiece also including injection means, whose function is to direct onto the blades of the moving wheel a compressed air flow whose pneumatic energy is converted into kinetic energy when the compressed air flow strikes the blades of the moving wheel, the handpiece further including a discharge pipe, arranged in the handpiece handle and through which air is discharged after striking the blades of the moving wheel, the handpiece being characterized in that the discharge pipe is at least facing the area in which the compressed air strikes the blades of the moving wheel.

According to a complementary feature of the invention, the section of the discharge pipe extends over at least the height of the moving wheel blades.

According to another feature of the invention, the compressed air injection means are arranged in the wall of the handpiece handle.

As a result of this feature, the present invention provides a compressed air handpiece in which the return of the compressed air, after it has struck the turbine blades, is greatly facilitated, which improves the conversion between the pneumatic energy of the compressed air and the kinetic energy of the turbine by facilitating the pressure drop between the moment when the compressed air penetrates the head of the handpiece and the moment when the compressed air exits the head. It is understood, in fact, that whereas part of the compressed air goes around and drives the turbine, the other part of the compressed air ricochets onto the turbine blades and creates turbulence in the handpiece head. This turbulence considerably impedes the conversion efficiency between pneumatic energy and kinetic energy. By arranging the discharge pipe at least facing the area in which the compressed air strikes the blades of the moving wheel, the present invention thus facilitates the evacuation of air which ricochets onto the turbine blades and thus makes it possible to considerably reduce turbulence in the turbine head.

According to yet another feature of the invention, the compressed air injection means take the form of an insert, inside which there is arranged a compressed air flow feed pipe, and which is placed inside the handpiece handle.

According to yet another feature of the invention, the insert is arranged inside the discharge pipe.

According to yet another feature of the invention, the insert is mounted coaxially inside the discharge pipe.

According to yet another feature of the invention, the insert is arranged so that the central axis of the compressed air flow extends in a tangential direction to the outer diameter of the moving wheel.

According to yet another feature of the invention, the compressed air flow feed pipe is formed of a first and a second rectilinear pipes arranged in the extension of each other, the second rectilinear pipe having a longitudinal axis of symmetry which extends in a tangential direction to the outer diameter of the moving wheel.

As a result of these features, the present invention provides a handpiece wherein the injection means take the form of an insert intended to be mounted inside the handpiece handle. The fact of using an independent part makes it possible to channel the air flow in a direction tangent to the outer diameter of the moving wheel more easily than in the case where the air feed pipe is machined by conventional techniques in the body of the handpiece. Indeed, in compressed air handpieces, the turbine is arranged in a head which is typically disposed inside the extension of a generally rectilinear gripping handle part inside which the compressed air feed pipe is machined. Unless complex and therefore not economically viable measures are taken, it is not possible to machine bent portions in the gripping handle part of the handpiece using conventional techniques. Consequently, the compressed air feed pipe must be machined slantwise relative to the longitudinal axis of symmetry of the handle part if the air flow is required to strike the turbine blades in a direction which is close to the tangent to the outer diameter of the moving wheel. However, it must also be possible to machine, in the handpiece handle, a discharge pipe through which the air is discharged after striking the blades of the moving wheel. The inclination of the compressed air feed pipe relative to the longitudinal axis of symmetry of the gripping handle part is thus necessarily limited since, otherwise, the compressed air feed pipe would open into the discharge pipe, which is technically unthinkable.

According to another advantage of the invention, the insert which serves to force the compressed air flow towards the blades of the moving wheel is mounted inside the discharge pipe arranged in the handpiece body and through which the air is discharged after striking the blades of the moving wheel. This arrangement facilitates the air return and thus greatly promotes the pressure drop between the pressure of the compressed air before it strikes the turbine blades and the pressure of the air exiting the handpiece head after striking the turbine blades. The higher the pressure drop, the better the conversion between the pneumatic energy of the compressed air and the kinetic energy of the turbine. This pressure drop is further amplified by the fact that the insert is mounted coaxially inside the discharge pipe. The diameter of the discharge pipe can thus be increased, which makes it possible to bring the air pressure inside the handpiece head down to values close to atmospheric pressure. Finally, the conversion efficiency between pneumatic energy and kinetic energy is further improved because the air flow occurs with minimal turbulence and thus minimal losses. Further, the operating noise of the handpiece is reduced and virtually no air is discharged into the patient's mouth.

According to another advantage of the invention, the injection means force the compressed air flow so that the compressed air flow strikes the blades of the moving turbine wheel in a tangential direction to the outer diameter of the moving wheel. Consequently, this ensures that maximum torque is exerted by the air flow on the turbine blades, which substantially increases the power provided by the turbine. By way of example, the power provided by current compressed air handpieces is on the order of 13 watts, whereas the measured power of a compressed air handpiece according to the invention is on the order of 20 watts. Therefore, with a compressed air handpiece according to the invention practitioners enjoy increased power, which allows them to work more quickly or to perform treatments which, until now, would have been difficult to achieve using a compressed air handpiece due to the insufficient power available.

The present invention also concerns a turbine for a compressed air handpiece for dental or surgical use, said turbine including a moving wheel from the periphery of which extend a plurality of regularly spaced blades, the turbine being characterized in that each of the blades is formed of a first surface, which extends from the outer diameter of the moving wheel and which leads to a second surface, which extends along a radius of the moving wheel.

According to a preferred embodiment of the invention, the first surface extends from the outer diameter of the moving wheel to a point on the radius of the moving wheel from which the second surface extends radially to the outer diameter of the moving wheel.

Finally, according to another feature of the invention, the blades are associated in pairs in a stepped manner, each blade being separated from its corresponding blade by a notch which extends in the direction of the compressed air flow, so that the air flow is divided into two equal parts at the moment it reaches the notch. The object of this notch is to reduce the transit time from one blade to the next in order to limit the mechanical power losses of the turbine.

The first surface leads the compressed air exiting the injection means towards the second surface. As the second surface extends along a radius of the moving wheel and the compressed air flow is channelled in a tangential direction to the outer diameter of the moving wheel, the compressed air flow falls perpendicularly onto the second surface of the blade and then turns back. The mechanical power provided by a turbine increases with the angle of deviation of the compressed air. In the case of the present invention, the angle of deviation of the compressed air is 180°, which corresponds to optimum conversion between the pneumatic energy of the compressed air and the kinetic energy of the turbine.

BRIEF DESCRIPTION OF THE DRAWINGS

Other features and advantages of the present invention will appear more clearly from the following detailed description of one embodiment of a compressed air handpiece according to the invention, this example being given merely by way of non-limiting illustration with reference to the annexed drawing, in which.

DETAILED DESCRIPTION OF AN EMBODIMENT OF THE INVENTION

The present invention proceeds from the general inventive idea which consists in taking any measures necessary to increase the mechanical power that can be provided by a compressed air handpiece. To this end, the present invention attempts to optimise the conversion efficiency between the pneumatic energy of the compressed air and the kinetic energy of the moving turbine wheel. Indeed, the mechanical power that the compressed air handpiece can deliver depends on this conversion efficiency. This conversion efficiency is, in particular, closely linked to the air flow conditions inside the turbine head. Indeed, it is known that, whereas part of the compressed air injected into the handpiece head drives and goes around the turbine, another part of the compressed air simply ricochets onto the turbine blades and thus tends to turn back creating turbulence in the handpiece head. By arranging the air discharge means at least in the area into which this air is injected, the present invention facilitates the evacuation of compressed air which ricochets onto the turbine blades and which tends to create turbulence in the handpiece head. Conversion efficiency between the pneumatic energy and kinetic energy is also linked to the angle at which the compressed air strikes the turbine blades. This is why, according to a first aspect, the present invention teaches creating the compressed air feed means in the form of an insert placed inside the handpiece. The fact of using an additional part enables the designer to enjoy much greater freedom as to the positioning of the insert than in the case where the designer should machine a compressed air feed pipe in the handpiece handle using conventional techniques. According to another aspect of the invention, the compressed air feed insert is placed coaxially inside the compressed air discharge pipe. This arrangement limits turbulence and thus facilitates the air return, which promotes the pressure drop between the compressed air pressure before it strikes the turbine blades and the air pressure when it exits the handpiece head after striking the turbine blades. The conversion efficiency between the pneumatic energy of the compressed air and the kinetic energy of the moving turbine wheel is thus also optimised. To achieve this result, the present invention also teaches channelling the compressed air flow in a tangential direction to the outer diameter of the turbine of the compressed air handpiece. Consequently, the compressed air flow strikes the turbine blades perpendicularly to their surface, which ensures that maximum torque is exerted by the air flow on the turbine blades and thus substantially increases the power provided by the turbine. Finally, the turbine blades are each formed of a first surface which extends from the outer diameter of the moving wheel and leads to a second surface which extends along a radius of the moving wheel away from the centre of the moving wheel. The compressed air thus falls perpendicularly onto the second surface of the blade and is driven backwards with a deviation of 180°. The greater the deviation angle of the compressed air flow, the greater the force exerted on the turbine blades. Finally, the operating noise of the turbine according to the invention is limited and work is performed almost at atmospheric pressure, so that very little air is discharged into the patient's mouth.

Figure 2:
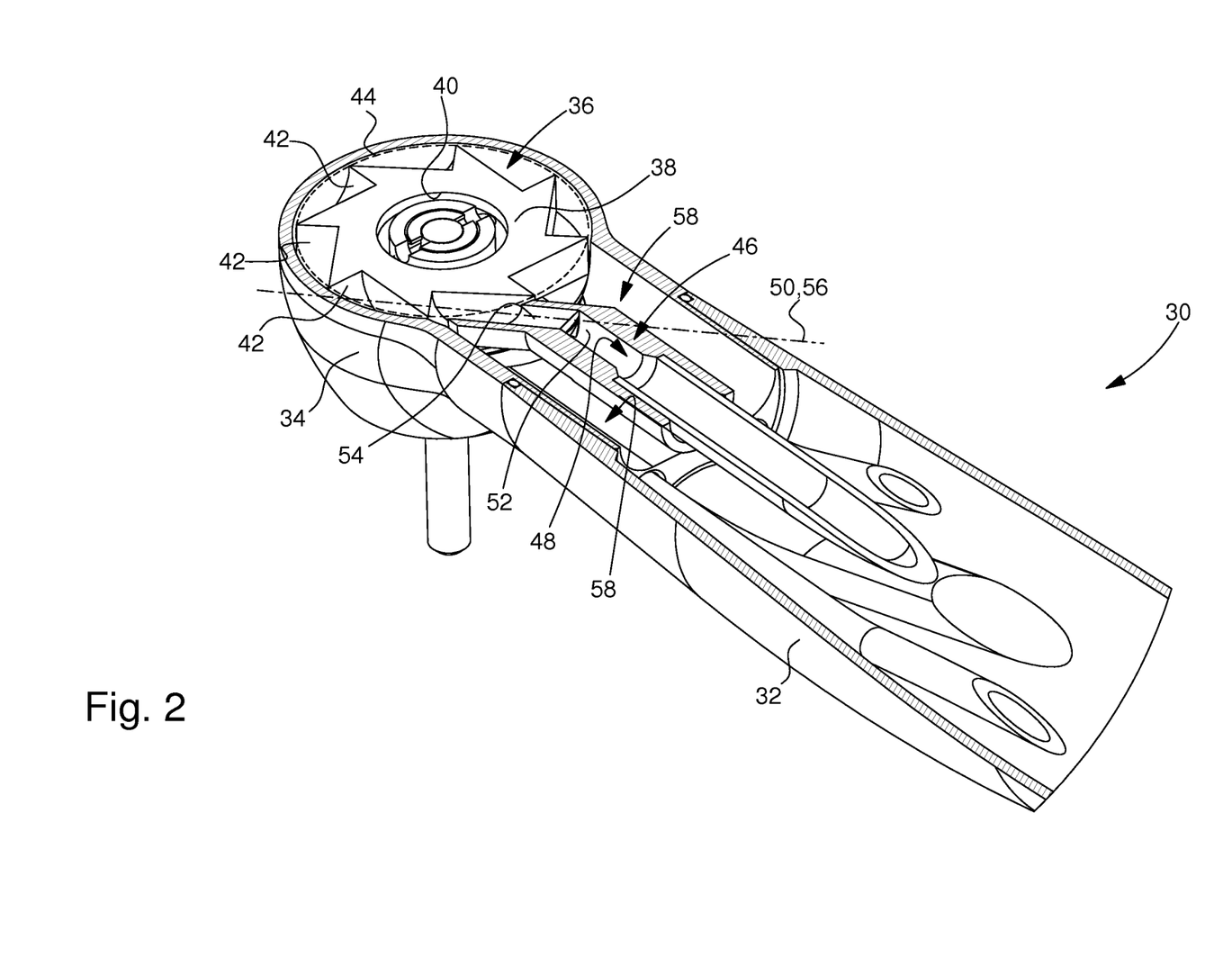
FIG. 2 is a cross-section along a horizontal plane longitudinally intersecting the handle and the head of a compressed air handpiece according to the invention.

FIG. 2 is a cross-section on a horizontal plane longitudinally intersecting the handle and the head of the compressed air handpiece according to the invention. Designated as a whole by the general reference numeral 30, the handpiece according to the invention includes a handle 32 which is connected to a head 34 which houses a turbine 36. Turbine 36 includes a moving wheel 38 from a periphery 40 of which extends a plurality of blades 42, which define an outer diameter 44 of moving wheel 38.

Handpiece 30 also includes injection means whose function is to direct onto blades 42 of moving wheel 38 a compressed air flow whose pneumatic energy is converted into kinetic energy when the compressed air flow strikes blades 42 of moving wheel 38.

To this end, the compressed air injection means take the form of an independent insert 46 mounted inside handpiece 30 and inside which there is arranged a compressed air flow feed pipe 48. In a preferred but non-limiting manner, pipe 48 is arranged so that the central axis 50 of the compressed air flow extends in a tangential direction to the outer diameter 44 of moving wheel 38. The present invention therefore provides a handpiece 30 wherein the injection means force the compressed air flow so that the compressed air flow strikes the blades 42 of moving wheel 38 of turbine 36 in a tangential direction to the outer diameter 44 of moving wheel 38. Consequently, this ensures that maximum torque is exerted by the air flow on blades 42 of turbine 36, which substantially increases the power provided by turbine 36.

According to a preferred but non-limiting embodiment of the invention, the compressed air flow feed pipe 48 is formed of a first and a second rectilinear pipe, respectively 52 and 54, arranged in the extension of each other, the longitudinal axis of symmetry 56 of the second rectilinear pipe 54 extending in a tangential direction to the outer diameter 44 of moving wheel 38.

According to yet another feature of the invention, insert 46, which serves to force the compressed air flow towards blades 42 of moving wheel 38, is mounted inside a discharge pipe 58 arranged in handle 32 of handpiece 30 and through which air is discharged after striking blades 42 of moving wheel 38. In a preferred but non-limiting manner, insert 46 is mounted coaxially inside discharge pipe 58.

The above arrangement greatly promotes the pressure drop between the compressed air pressure before it strikes blades 42 of turbine 36 and the pressure of the air exiting head 34 of handpiece 30 after striking blades 42 of turbine 36. The higher the pressure drop, the better the conversion between the pneumatic energy of the compressed air and the kinetic energy of turbine 36. This pressure drop is further amplified by the fact that insert 46 is mounted coaxially inside discharge pipe 58. The diameter of discharge pipe 58 can thus be increased, which facilitates the air return and makes it possible to bring the air pressure in head 34 of handpiece 30 down to values close to atmospheric pressure. Finally, the conversion efficiency between pneumatic energy and kinetic energy is further improved because the air flow occurs with minimal turbulence and thus minimal losses. Further, the operating noise of the handpiece 30 is reduced and virtually no air leaks into the patient's mouth occurs given that the pressure in head 34 of turbine 36 is close to atmospheric pressure.

Figure 3:
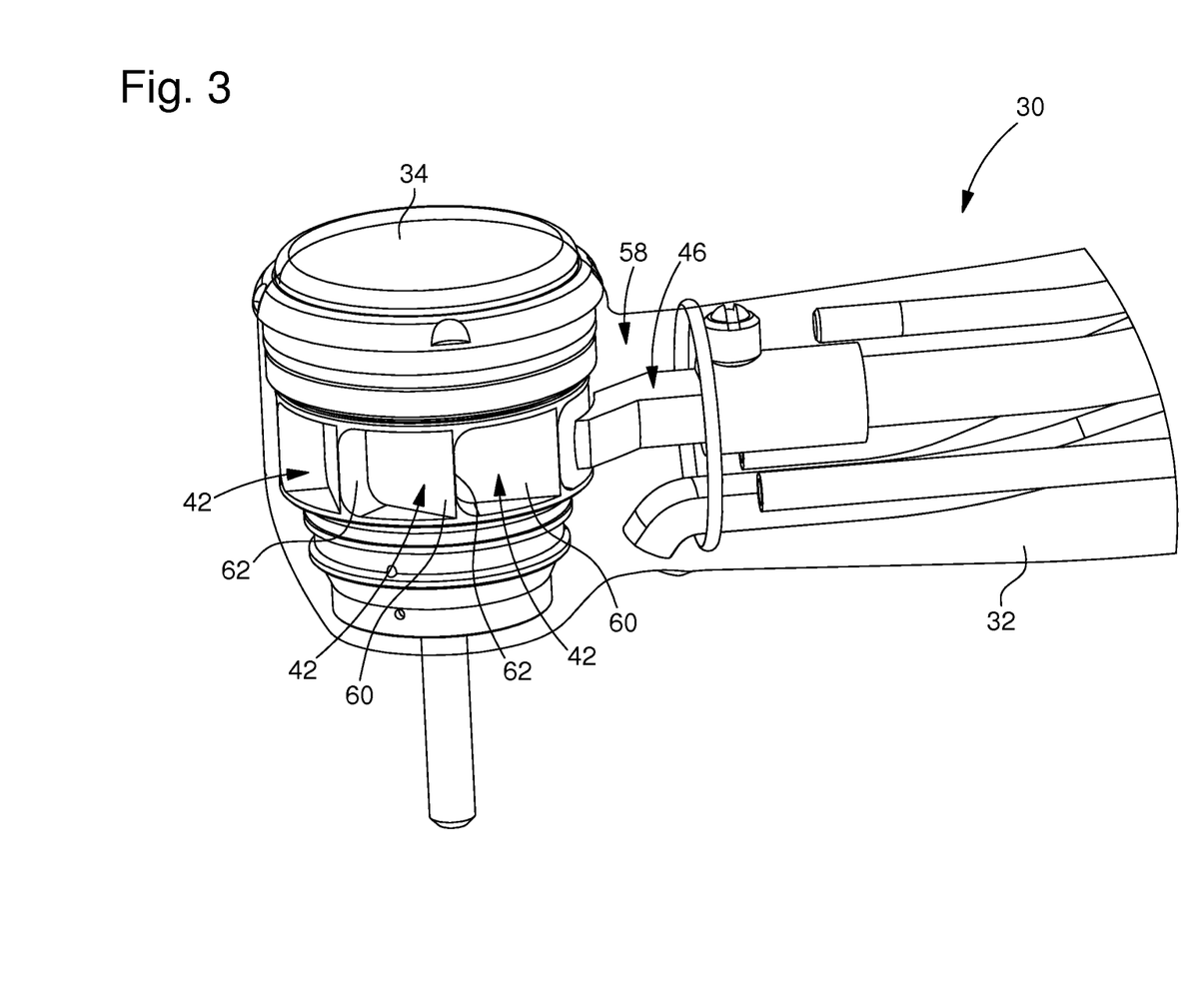
FIG. 3 is a partially transparent side view of the head and the handle of the compressed air handpiece according to the invention.

FIG. 3 is a partially transparent side view of head 34 and of handle 32 of compressed air handpiece 30 according to the invention. As revealed by an examination of this Figure, each of blades 42 of turbine 36 is formed of a first surface 60 which extends from the outer diameter 44 of moving wheel 38 and which leads to a second surface 62 which extends radially along a radius R of moving wheel 38.

Figure 4:
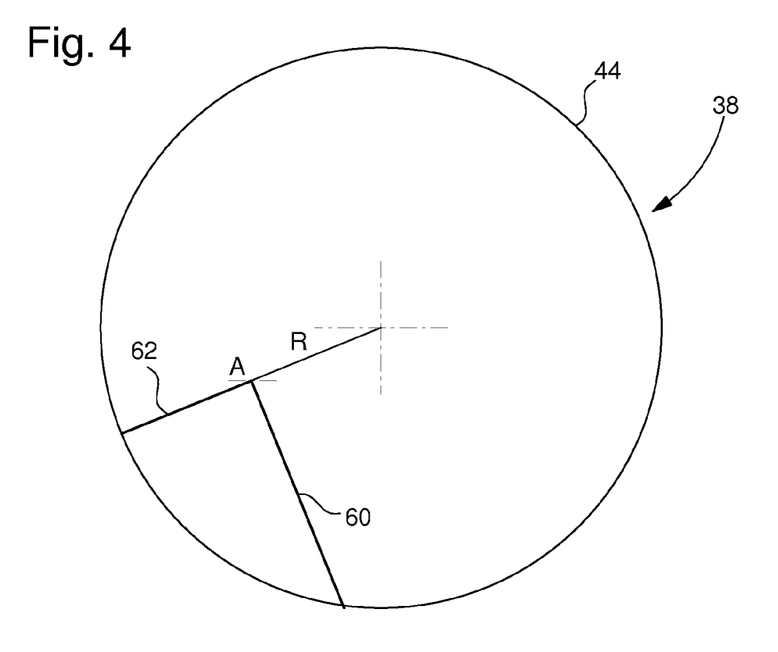
FIG. 4 is a schematic diagram illustrating the first and second surfaces of a turbine blade.

More specifically (see also FIG. 4), the first surface 60 extends from the outer diameter 44 of moving wheel 38 to a point A on the radius R of moving wheel 38 from which the second surface 62 extends to the outer diameter 44 of moving wheel 38. First surface 60 is advantageously plane, while second surface 62 has a profile in the shape of an arc of a circle tangential to the radius R of moving wheel 38. Preferably, first surface 60 forms a right angle with second surface 62.

Finally (see FIG. 5), according to a preferred variant embodiment of the invention, blades 42 are associated in pairs in a stepped manner, each blade 42 being separated from the blade associated therewith by a notch 64 which extends in the direction of the compressed air flow F, so that the air flow F is divided into two equal parts F 1 at the moment it reaches notch 64. The object of this notch 64 is to reduce the transit time from one blade to the next so as to limit mechanical power losses in turbine 36.

Figure 5:
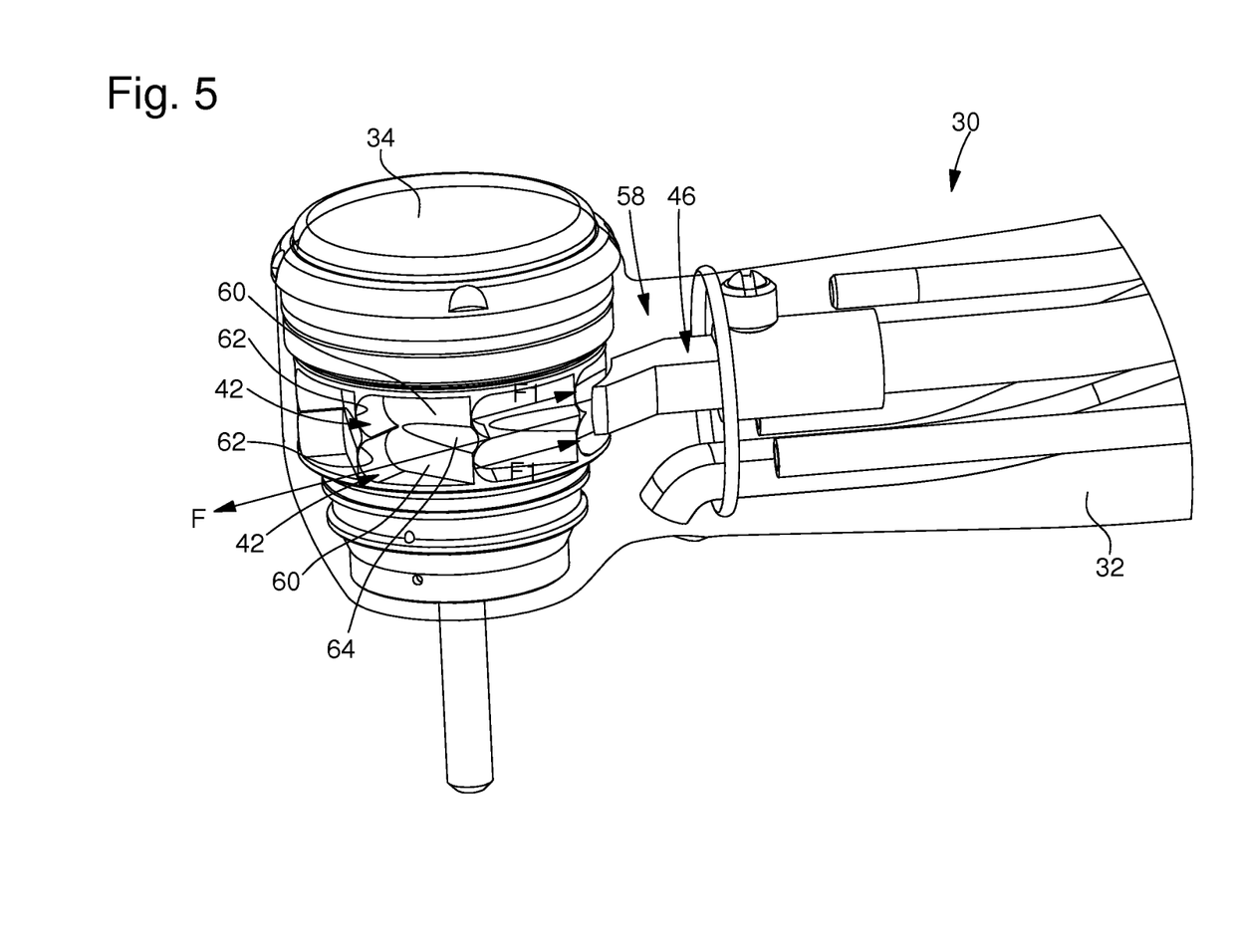
FIG. 5 illustrates an improved variant embodiment of the turbine according to the invention.

From the foregoing it is clear that first surface 60 of blades 42 leads the compressed air exiting the injection means towards second surface 62. Since second surface 62 extends along a radius R of moving wheel 38 and the compressed air flow is channelled in a tangential direction to the outer diameter 44 of moving wheel 38, the compressed air flow falls perpendicularly onto second surface 62 of blade 42 and then turns back, deflected by the profile in the shape of an arc of a circle of second surface 62. The mechanical power provided by a turbine increases with the angle of deviation of the compressed air. In the case of the present invention, the deviation angle of the compressed air is 180°, which corresponds to optimum conversion between the pneumatic energy of the compressed air and the kinetic energy of turbine 36.

Figure 6:
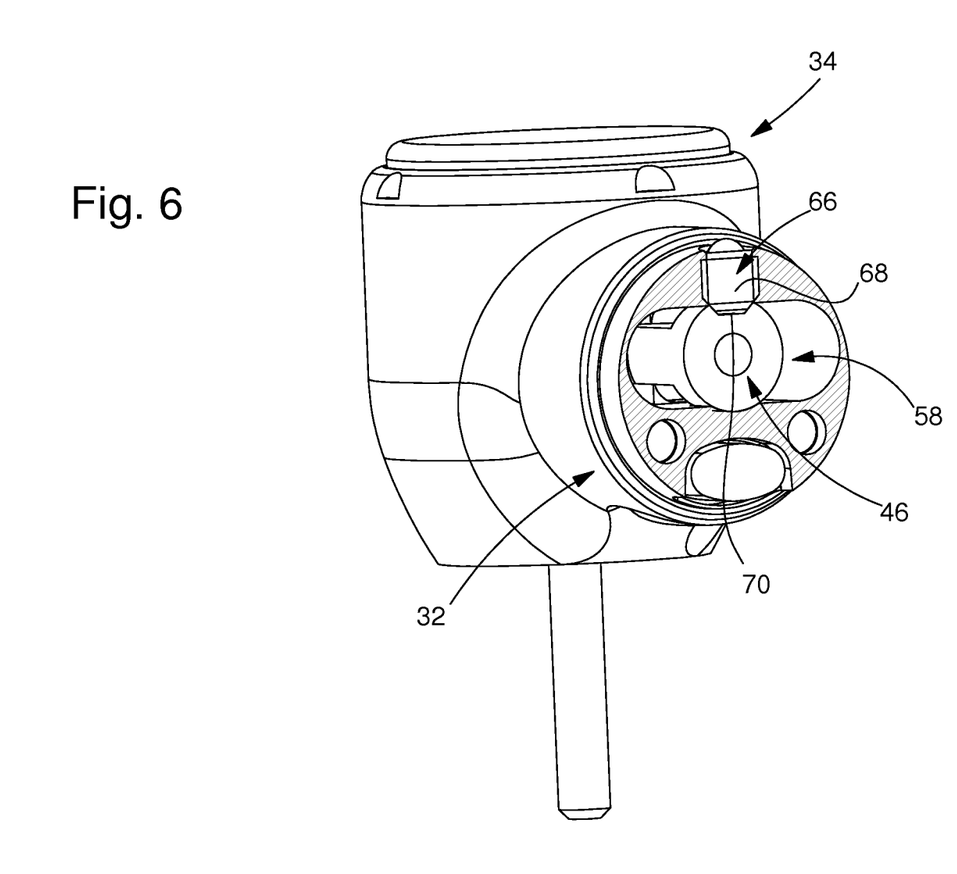
FIG. 6 is a view of the back of the compressed air handpiece head according to the invention, in the area where the handpiece head is connected to the handpiece handle.
Figure 7:
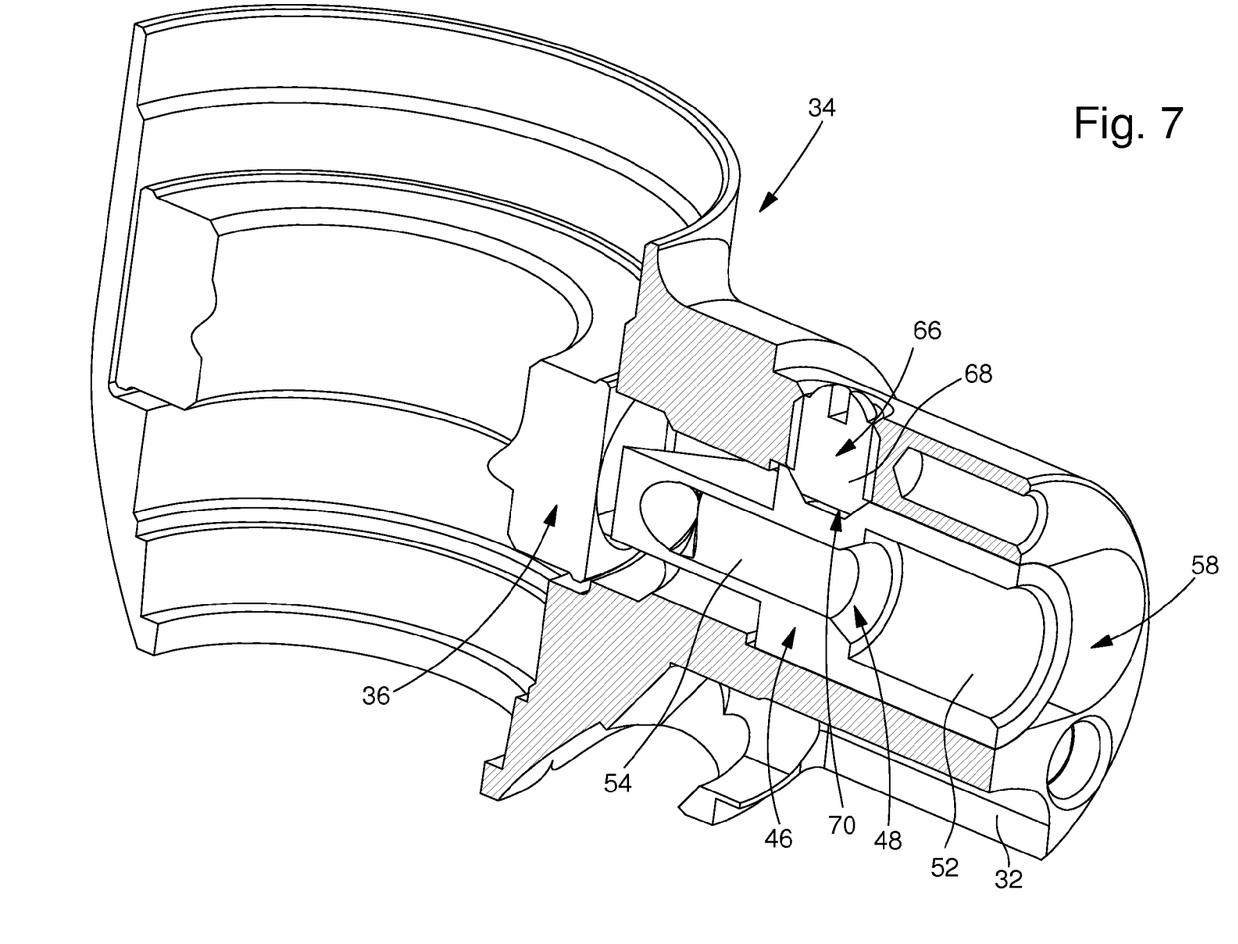
FIG. 7 is a cross-section in a vertical plane passing through the longitudinal axis of symmetry of the head and a portion of the handle of the compressed air handpiece according to the invention.

FIG. 6 is a rear view of head 34 of compressed air handpiece 30 according to the invention, in the area where head 34 of handpiece 30 is connected to handle 32 of handpiece 30; and FIG. 7 is a cross-sectional view in a vertical plane passing through the longitudinal axis of symmetry of head 34 and of a portion of handle 32 of compressed air handpiece 30 according to the invention. These two Figures clearly show that insert 46, which serves to force the compressed air flow towards blades 42 of moving wheel 48, is mounted inside discharge pipe 58 arranged in handle 32 of handpiece 30 and through which air is discharged after striking blades 42 of moving wheel 38. Preferably, insert 46 is mounted coaxially inside discharge pipe 58. Consequently, discharge pipe 58 is as large as possible and is as close as possible to the compressed air flow feed pipe 58, which facilitates the air return and maximises the pressure drop, so that the conversion between the pneumatic energy of the compressed air and the kinetic energy of turbine 36 is optimised. An examination of FIG. 7 also reveals that the section S of discharge pipe 58 extends over at least the height H of blades 42 of moving wheel 38.

According to yet another feature of the invention, insert 46 includes means of adjusting the position of the insert inside handle 32 of handpiece 30. According to an example given purely by way of non-limiting illustration, the adjustment means include an adjusting screw 66 a foot 68 of which is received in a seat 70 arranged at the periphery of insert 46. Seat 70 could be replaced by two flat portions.

It goes without saying that this invention is not limited to the embodiment that has just been described and that various simple modifications and variants can be envisaged by those skilled in the art without departing from the scope of the invention as defined by the annexed claims. In particular, the present invention teaches that the means of injecting compressed air preferably take the form of an independent insert 46 mounted inside handpiece 30 and inside which is arranged a compressed air feed pipe 48. The object of this solution is to overcome the problems that those skilled in the art would encounter if they sought to machine slantwise a compressed air feed pipe using conventional techniques in the, for example, stainless steel handle of a handpiece. Another solution to the problem raised by the invention exists however. Indeed, in the case where the handpiece is made by moulding a material such as a ceramic, it may be possible to envisage devising manufacturing moulds such that the feed pipe extends coaxially inside the discharge pipe. It is also possible to envisage making the handpiece by the injection of a plastic material or a metallic material, this latter technique being better known as Metal Injection Molding or MIM.

Figure 8:
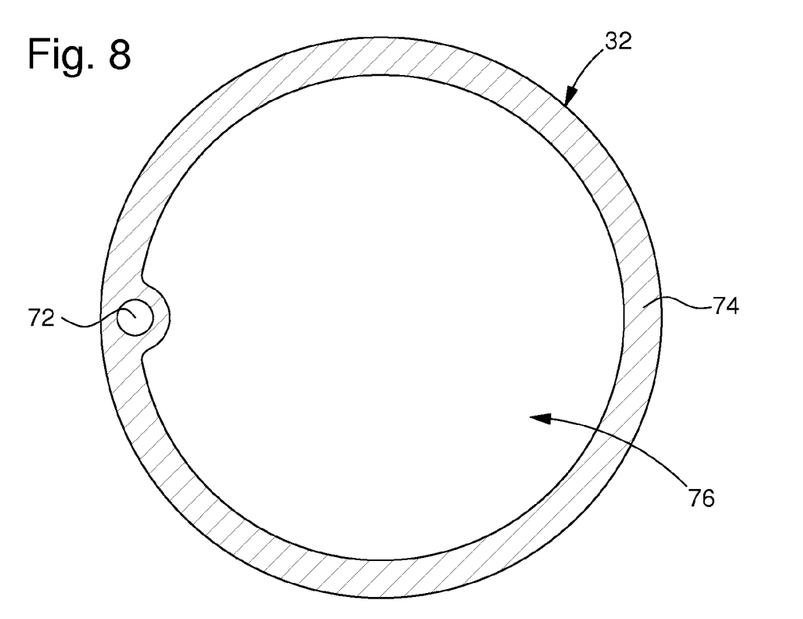
FIG. 8 is a schematic diagram of a variant embodiment of the compressed air handpiece according to the invention.

According to a variant embodiment, the compressed air injection means 72 are arranged in the wall 74 of handle 32 of handpiece 30 and the compressed air discharge means 76 occupy most of the section of handle 32. This type of arrangement can typically be obtained using three-dimensional printing techniques.

What is claimed is:

1. A compressed air handpiece comprising:
    a handle connected to a head housing a turbine, wherein the turbine includes a moving wheel from a periphery of which extend a plurality of blades defining an outer diameter of the moving wheel, wherein
    the handpiece also includes a compressed air injector to direct onto the blades of the moving wheel a compressed air flow whose pneumatic energy is converted into kinetic energy when the compressed air flow strikes the blades of the moving wheel, wherein
    the handpiece further includes a discharge pipe, arranged in the handle of the handpiece and through which air is discharged after striking the blades of the moving wheel, wherein an opening of the discharge pipe into the head is at least facing an area in which the compressed air flow strikes the blades of the moving wheel, and wherein
    the compressed air injector extends inside of the discharge pipe at least at the opening of the discharge pipe into the head, and the opening of the discharge pipe into the head completely surrounds the compressed air injector.

2. The compressed air handpiece according to claim 1, wherein a section of the discharge pipe extends over at least a height of the blades of the moving wheel.

3. The compressed air handpiece according to claim 1, wherein the compressed air injector is arranged in a wall of the handle of the handpiece.

4. The compressed air handpiece according to claim 2, wherein the compressed air injector is arranged in a wall of the handle of the handpiece.

5. The compressed air handpiece according to claim 1, wherein the compressed air injector comprises an insert inside which is arranged a compressed air flow feed pipe and which is placed inside the handle of the handpiece.

6. The compressed air handpiece according to claim 2, wherein the compressed air injector comprises an insert inside which is arranged a compressed air flow feed pipe and which is placed inside the handle of the handpiece.

7. The compressed air handpiece according to claim 3, wherein the compressed air injector comprises an insert inside which is arranged a compressed air flow feed pipe and which is placed inside the handle of the handpiece.

8. The compressed air handpiece according to claim 4, wherein the compressed air injector comprises an insert inside which is arranged a compressed air flow feed pipe and which is placed inside the handle of the handpiece.

9. The compressed air handpiece according to claim 5, wherein the insert is arranged inside the discharge pipe.

10. The compressed air handpiece according to claim 6, wherein the insert is arranged inside the discharge pipe.

11. The compressed air handpiece according to claim 7, wherein the insert is arranged inside the discharge pipe.

12. The compressed air handpiece according to claim 8, wherein the insert is arranged inside the discharge pipe.

13. The compressed air handpiece according to claim 9, wherein the insert is mounted coaxially inside the discharge pipe.

14. The compressed air handpiece according to claim 10, wherein the insert is mounted coaxially inside the discharge pipe.

15. The compressed air handpiece according to claim 11, wherein the insert is mounted coaxially inside the discharge pipe.

16. The compressed air handpiece according to claim 12, wherein the insert is mounted coaxially inside the discharge pipe.

17. The compressed air handpiece according to claim 5, wherein the insert is arranged so that a central axis of the compressed air flow extends in a tangential direction to the outer diameter of the moving wheel.

18. The compressed air handpiece according to claim 5, wherein the compressed air flow feed pipe is formed of a first rectilinear pipe and a second rectilinear pipe arranged in an extension of each other, wherein the second rectilinear pipe has a longitudinal axis of symmetry which extends in a tangential direction to the outer diameter of the moving wheel.

19. The compressed air handpiece according to claim 5, wherein the insert includes a mechanism to adjust a position of the insert inside the handle of the handpiece.

20. The compressed air handpiece according to claim 19, wherein the adjustment mechanism includes either a seat to receive an adjusting screw or two flat portions.

21. The compressed air handpiece according to claim 1, wherein each of the blades of the turbine is formed of a first surface extending from the outer diameter of the moving wheel and leading to a second surface extending along a radius of the moving wheel.

22. The compressed air handpiece according to claim 21, wherein the first surface extends from the outer diameter of the moving wheel to a point on the radius of the moving wheel from which the second surface extends to the outer diameter of the moving wheel.

23. The compressed air handpiece according to claim 22, wherein the first surface is planar, and the second surface has a profile in a shape of an arc of a circle tangential to the radius of the moving wheel.

24. The compressed air handpiece according to claim 1, wherein the blades are associated in pairs in a stepped manner, wherein each blade is separated from a blade associated therewith by a notch which extends in a direction of the compressed air flow, so that the compressed air flow is divided into two equal parts at a moment when the compressed air flow reaches the notch.

25. The compressed air handpiece according to claim 1, wherein an end of the compressed air injector at the opening of the discharge pipe into the head is angled relative to an extension direction of the handle.

* * * * *

UNITED STATES PATENT AND TRADEMARK OFFICE
CERTIFICATE OF CORRECTION

PATENT NO. : 9,877,797 B2  
APPLICATION NO. : 14/533726  
DATED : January 30, 2018  
INVENTOR(S) : Laurent Farine Page 1 of 1

It is certified that error appears in the above-identified patent and that said Letters Patent is hereby corrected as shown below:

On the Title Page

Item (71), Applicant, Column 1, Line 1, delete "Bienne" and insert --Bienne 6--.

Item (73), Assignee, Column 1, Line 1, delete "Bienne" and insert --Bienne 6--.

Signed and Sealed this  
Second Day of June, 2020

Andrei Iancu  
*Director of the United States Patent and Trademark Office*